(12) United States Patent
Clark et al.

(10) Patent No.: US 8,690,764 B2
(45) Date of Patent: Apr. 8, 2014

(54) ENDOSCOPE CLEANER

(75) Inventors: Charlotte Adele Clark, Cambridge (GB); Cormac O'Prey, Bishops Stortford (GB); Alistair Ian Fleming, Lower Cambourne (GB); Nicholas John Collier, Burwell (GB); Robert James Applegate, Wallingfort, CT (US)

(73) Assignee: Covidien LP, Mansfield, MA (US)

( * ) Notice: Subject to any disclaimer, the term of this patent is extended or adjusted under 35 U.S.C. 154(b) by 151 days.

(21) Appl. No.: 13/245,020

(22) Filed: Sep. 26, 2011

(65) Prior Publication Data

US 2012/0101337 A1    Apr. 26, 2012

Related U.S. Application Data

(60) Provisional application No. 61/394,814, filed on Oct. 20, 2010.

(51) Int. Cl.
*A61B 1/12* (2006.01)
*A61B 1/00* (2006.01)

(52) U.S. Cl.
USPC .......................................... 600/157; 600/156

(58) Field of Classification Search
USPC .......................... 600/157, 159, 169, 104, 114; 604/99.04, 167.01–167.06
See application file for complete search history.

(56) References Cited

U.S. PATENT DOCUMENTS

| | | | |
|---|---|---|---|
| 4,281,646 A | 8/1981 | Kinoshita | |
| 4,919,113 A | 4/1990 | Sakamoto et al. | |
| 4,941,872 A | 7/1990 | Felix et al. | |
| 5,127,909 A | 7/1992 | Shichman | |
| 5,207,213 A | 5/1993 | Auhll et al. | |
| 5,274,874 A | 1/1994 | Cercone et al. | |
| 5,313,934 A | 5/1994 | Wiita et al. | |
| 5,337,730 A | 8/1994 | Maguire | |
| 5,354,302 A | 10/1994 | Ko | |
| 5,382,297 A | 1/1995 | Valentine et al. | |
| 5,392,766 A * | 2/1995 | Masterson et al. | 600/157 |
| 5,400,767 A | 3/1995 | Murdoch | |
| 5,505,707 A * | 4/1996 | Manzie et al. | 604/131 |
| 5,514,084 A | 5/1996 | Fisher | |
| 5,630,795 A | 5/1997 | Kuramoto et al. | |
| 5,735,792 A | 4/1998 | Vanden Hoek et al. | |
| 5,755,782 A | 5/1998 | Love et al. | |
| 5,931,833 A | 8/1999 | Silverstein | |
| 5,944,654 A * | 8/1999 | Crawford | 600/157 |

(Continued)

FOREIGN PATENT DOCUMENTS

DE    2008 059633    6/2010
EP    1323373    7/2003

(Continued)

OTHER PUBLICATIONS

European Search Report dated Oct. 10, 2012 for copending European Application No. 12154377.

*Primary Examiner* — Anhtuan T Nguyen
*Assistant Examiner* — Timothy J Neal

(57) ABSTRACT

An instrument for cleaning a scope lens having an elongated sheath having proximal and distal end portions and a sheath interior and exterior. The sheath interior is dimensioned and configured to slidingly receive a scope therein. A fluid conduit transports fluid and has a fluid discharge opening to deliver fluid to the lens of the scope, the conduit coupled to the sheath exterior.

16 Claims, 7 Drawing Sheets

(56) References Cited

U.S. PATENT DOCUMENTS

| | | |
|---|---|---|
| 6,354,992 B1 | 3/2002 | Kato |
| 6,387,044 B1 | 5/2002 | Tachibana et al. |
| 6,682,165 B2 | 1/2004 | Yearout |
| 6,755,782 B2 | 6/2004 | Ogawa |
| 6,923,759 B2 | 8/2005 | Kasahara et al. |
| 7,300,445 B2 | 11/2007 | Adams |
| 7,316,683 B2 | 1/2008 | Kasahara et al. |
| 7,339,341 B2 | 3/2008 | Oleynikov et al. |
| 7,530,984 B2 | 5/2009 | Sonnenschein et al. |
| 7,596,828 B2 | 10/2009 | Evdokimo |
| 7,959,561 B2 | 6/2011 | Akui et al. |
| 2002/0022762 A1 | 2/2002 | Beane et al. |
| 2002/0065450 A1 | 5/2002 | Ogawa |
| 2003/0073955 A1 | 4/2003 | Otawara |
| 2006/0293559 A1* | 12/2006 | Grice et al. ............... 600/102 |
| 2007/0208220 A1 | 9/2007 | Carter |
| 2007/0208221 A1 | 9/2007 | Kennedy, II et al. |
| 2007/0213667 A1 | 9/2007 | Prusmack |
| 2007/0282253 A1* | 12/2007 | Sasaki ............... 604/93.01 |
| 2007/0282356 A1 | 12/2007 | Sonnenschein et al. |
| 2008/0015618 A1 | 1/2008 | Sonnenschein et al. |
| 2008/0058852 A1 | 3/2008 | Ihde |
| 2008/0188715 A1 | 8/2008 | Fujimoto |
| 2008/0319266 A1 | 12/2008 | Poll et al. |
| 2009/0005799 A1 | 1/2009 | Franer et al. |
| 2009/0049627 A1 | 2/2009 | Kritzler |
| 2009/0105543 A1 | 4/2009 | Miller et al. |
| 2009/0112065 A1 | 4/2009 | Harrel |
| 2009/0234193 A1 | 9/2009 | Weisenburgh, III et al. |
| 2009/0240111 A1 | 9/2009 | Kessler et al. |
| 2009/0264703 A1 | 10/2009 | Pribanic |
| 2009/0270681 A1 | 10/2009 | Moreno et al. |
| 2009/0270685 A1 | 10/2009 | Moreno et al. |
| 2009/0270686 A1 | 10/2009 | Duke et al. |
| 2009/0270813 A1 | 10/2009 | Moreno et al. |
| 2009/0270817 A1 | 10/2009 | Moreno et al. |
| 2009/0270818 A1* | 10/2009 | Duke ............... 604/272 |
| 2010/0022958 A1 | 1/2010 | Moreno et al. |
| 2010/0030031 A1 | 2/2010 | Goldfarb et al. |
| 2010/0174144 A1 | 7/2010 | Hsu et al. |
| 2010/0256453 A1 | 10/2010 | Hammond et al. |
| 2011/0230716 A1 | 9/2011 | Fujimoto |

FOREIGN PATENT DOCUMENTS

| | | |
|---|---|---|
| EP | 1210904 | 6/2005 |
| EP | 1911409 | 4/2008 |
| JP | 2005/040184 | 2/2005 |
| JP | 2005 052229 | 3/2005 |
| JP | 2007 105314 | 4/2007 |
| JP | 2007/130167 | 5/2007 |
| JP | 2008/132282 | 6/2008 |
| JP | 2008/279202 | 11/2008 |
| JP | 2010/022758 | 2/2010 |
| WO | WO 98/24359 | 6/1998 |
| WO | WO-2008/153841 | 12/2008 |

\* cited by examiner

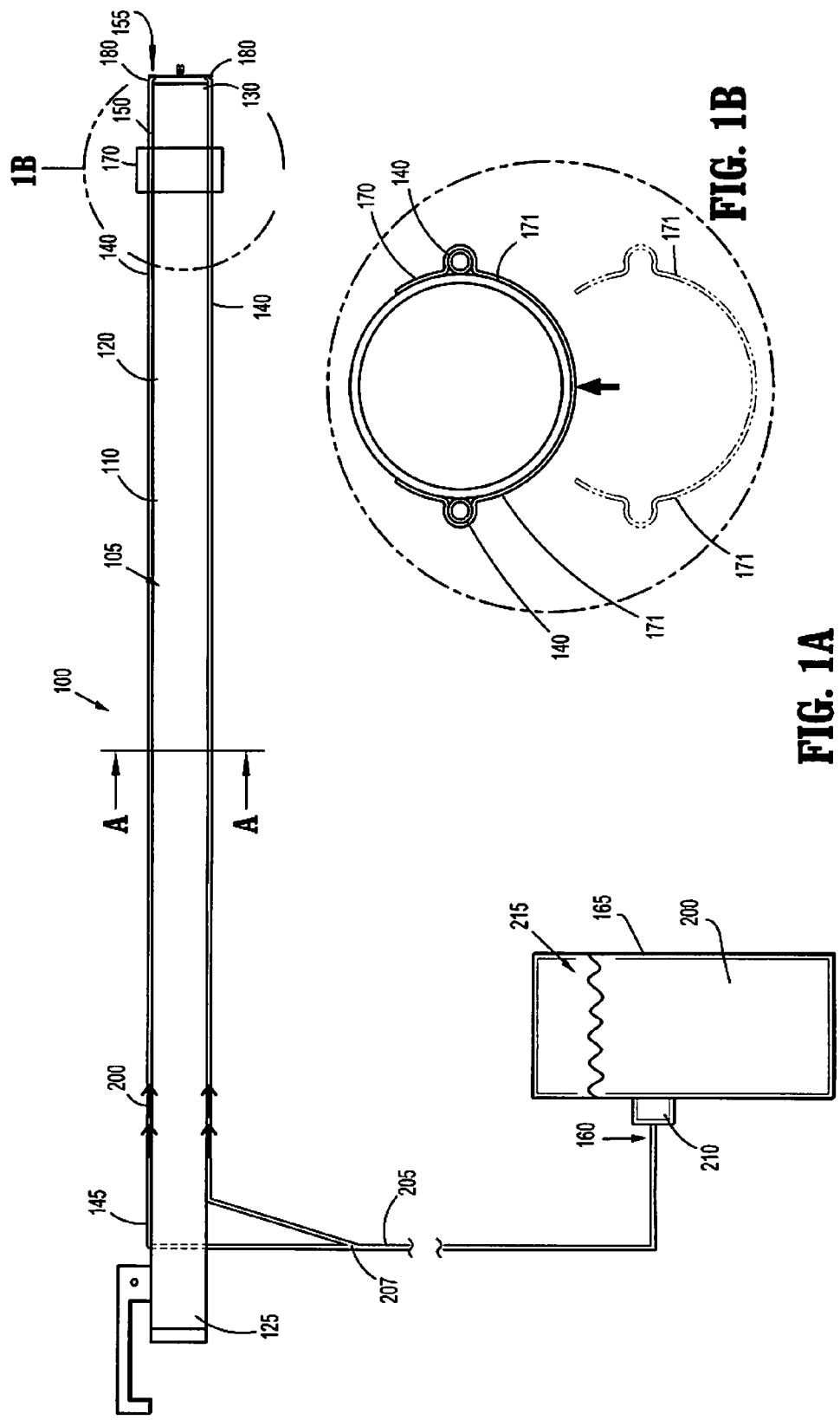

ENDOSCOPE CLEANER

This application claims priority from provisional application Ser. No. 61/394,814, filed Oct. 20, 2010, the entire contents of which are incorporated herein by reference.

BACKGROUND

1. Technical Field

The present disclosure relates to a cleaning apparatus configured to remove debris from the lens of a minimally invasive viewing instrument.

2. Background of Related Art

Minimally invasive surgery has become increasingly popular in recent years. Minimally invasive surgery eliminates the need to cut a large incision in a patient, thereby reducing discomfort, recovery time, and many of the deleterious side effects associated with traditional open surgery. Minimally invasive viewing instruments, e.g., laparoscopes and endoscopes, are optic instruments to facilitate the viewing of internal tissues and/or organs.

Laparoscopic surgery involves the placement of a laparoscope in a small incision in the abdominal wall of a patient to view the surgical site. Endoscopic surgery involves the placement of an endoscope in a naturally occurring orifice, e.g., mouth, nose, anus, urethra, and vagina to view the surgical site. Other minimally invasive surgical procedures include video assisted thoracic surgery and cardiovascular surgery conducted through small incisions between the ribs. These procedures also utilize scopes to view the surgical site.

A typical minimally invasive viewing instrument, e.g., a laparoscope or an endoscope, includes a housing, an elongated lens shaft extending from one end of the housing, and a lens that is provided in the distal end of the lens shaft. A camera viewfinder extends from the other end of the housing. A camera is connected to the housing and transmits images of the surgical field viewed through the lens to a monitor on which the images are displayed. During a surgical procedure, the distal end portion of the lens shaft is extended into the patient, while the proximal end portion of the lens shaft, the housing and the camera viewfinder remain outside the patient. In this manner, the laparoscope/endoscope is positioned and adjusted to view particular anatomical structures in the surgical field on the monitor.

During insertion of an endoscope or a laparoscope into the body and during the surgical procedure, debris, e.g., organic matter and moisture, may be deposited on the lens of the endoscope. The buildup of debris and condensation on the lens impairs visualization of the surgical site, and often necessitates cleaning of the lens.

SUMMARY

The present disclosure is generally related to an instrument for cleaning the lens of a medical viewing instrument, such as an endoscope, during a minimally invasive surgical procedure. In one aspect of the present disclosure, an instrument for cleaning the lens of a surgical scope is provided comprising an elongated sheath with proximal and distal end portions and having an interior and exterior and a fluid conduit for transporting fluid. The interior is dimensioned and configured to slidingly receive a scope therein. The fluid conduit has a fluid discharge opening to deliver fluid to the lens of the scope and is coupled to the sheath exterior.

Preferably, the instrument further includes a roller mechanism coupled to the distal portion of the sheath exterior and includes at least one movable wiping arm. The roller mechanism can in some embodiments be configured such that when the roller mechanism is in a cleaning position, the fluid conduit is in the dispensing state. The roller mechanism can be further configured such that when the roller mechanism is in a non-cleaning position, the fluid conduit is in the non-dispensing state.

The instrument may further comprise a wiping arm operatively connected to the sheath wherein insertion of the scope actuates the wiping arm. In some embodiments, advancement of the scope with respect to the sheath automatically discharges fluid through the discharge opening of the fluid conduit.

In some embodiments, the roller mechanism is in the non-cleaning position when the scope retracts inside the elongated sheath interior.

An attachment clip can be provided to attach the fluid conduit to the elongated sheath exterior.

The roller mechanism can include first and second wiping arms extending from a ring like member, and the wiping arms can move transversely over the scope lens.

In some embodiments, the instrument includes a pump configured to switch between first and second positions, the first position being to deliver fluid through the fluid discharge opening and the second position being to close the discharge opening.

The present disclosure provides in another aspect an instrument for cleaning a lens of a surgical scope comprising an elongated sheath with proximal and distal end portions and an interior and exterior and a pair of wiping arms supported by the sheath. The arms are movable from a first position adjacent one another to a second position spaced from each other. The arms are movable from the first to the second position upon contact by the lens of the scope inserted through the interior of the sheath.

In some embodiments, the wiping arms extend from a ring-like member positioned at a distal end portion of the sheath. The sheath preferably includes a fluid conduit for delivering a cleaning fluid to a lens of a scope inserted through the sheath.

In some embodiments, a fluid discharge nozzle communicates with the fluid conduit.

In some embodiments, movement of the wiping arms opens a valve for delivering cleaning fluid to a lens.

BRIEF DESCRIPTION OF THE DRAWINGS

The above and other aspects, features, and advantages of the present disclosure will become more apparent in light of the following detailed description when taken in conjunction with the accompanying drawings in which:

FIG. 1A is a schematic view of a scope lens cleaner according to an embodiment of the present disclosure;

FIG. 1B is close up view of the area of detail of FIG. 1A;

DETAILED DESCRIPTION

Figures 2A, 2B:
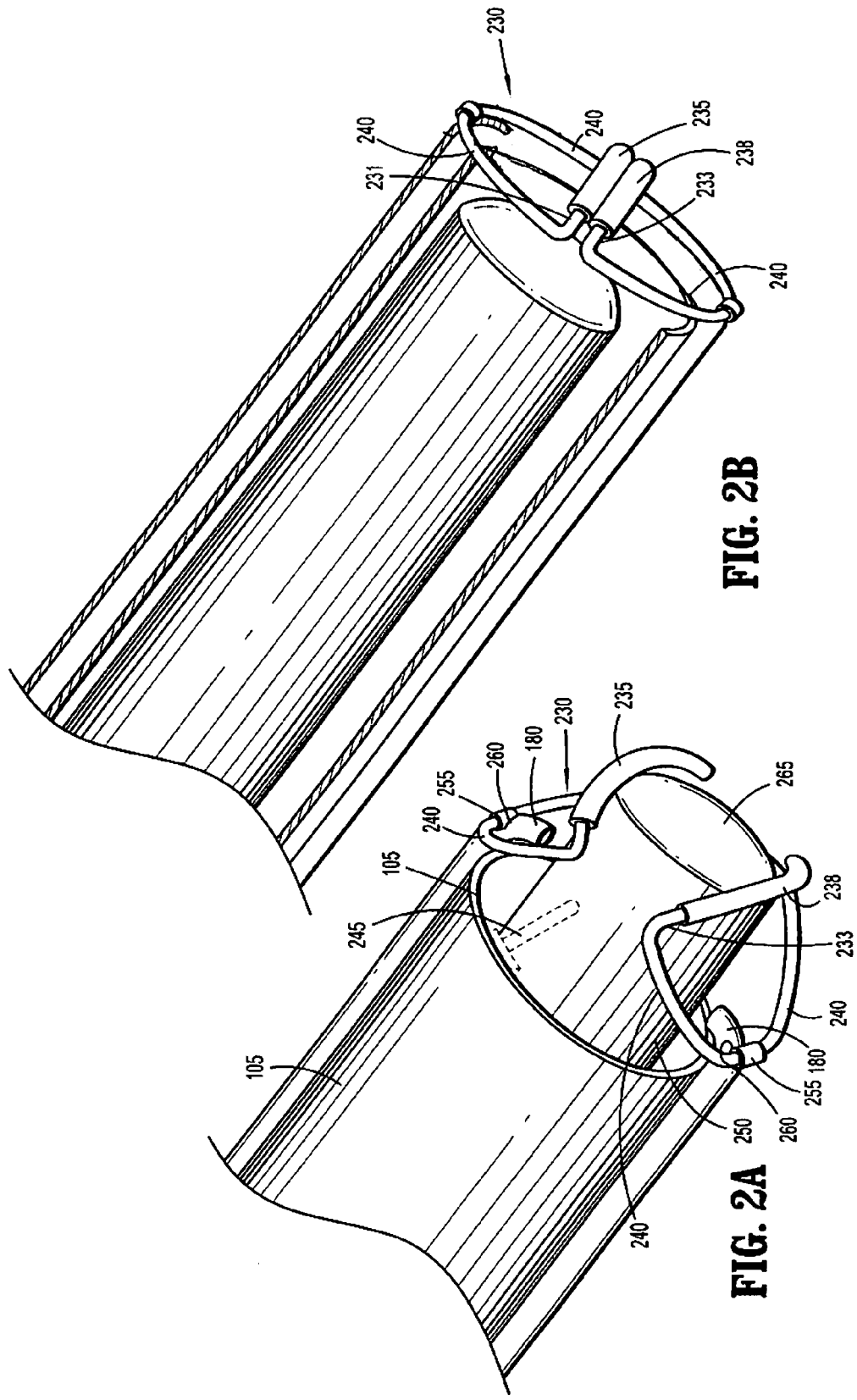
FIGS. 2A-2B are enlarged perspective views of the scope lens cleaner of FIG. 1A shown in different positions.

An endoscope typically includes an endoscope housing or body which can be rigid or flexible, depending on its surgical application. A camera viewfinder, e.g. an eyepiece, is located at a proximal (imaging) end of the scope housing. A lens is provided at the distal end of the scope body.

In typical use of the endoscope, the viewfinder is adapted to sight images of a surgical field in the patient, e.g. an abdominal cavity, thoracic cavity, etc., as the position of the scope is adjusted to view a particular anatomical structure or structures in the surgical field. The camera is adapted to receive images of the surgical field sighted through the lens and transmit the images to an external monitor that is connected to the camera and on which the images of the surgical field are displayed. That is, a visual display device is operatively connected to the eyepiece to convert the optical signal into a video signal to produce a video image on the monitor (or for storage on select media). Accordingly, the monitor enables a surgical team to view the anatomical structure or structures in the surgical field inside the patient as the surgical procedure is carried out using minimally invasive or endoscopic surgical instruments. Throughout the surgical procedure, condensation, smoke particles, biological tissue or matter has a tendency to contact and build up on the lens of the scope. This tends to obscure the images of the surgical field as they are displayed on the monitor.

The instrument of the present disclosure enables cleaning of the scope lens during the surgical procedure to maintain a clear image without having to remove the scope from the patient's body.

Particular embodiments of the present disclosure will be described herein with reference to the accompanying drawings. In the figures and in the description that follows, in which like reference numerals identify similar or identical elements, the term "proximal" will refer to the end of the apparatus that is closer to the operator during use, while the term "distal" will refer to the end that is further from the operator during use.

Figure 4:
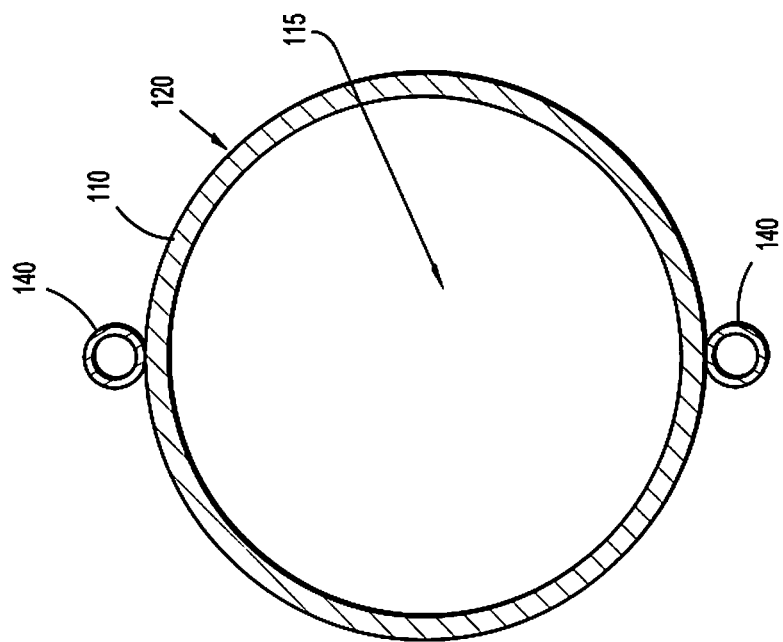
FIG. 4 is a cross-sectional view taken along section lines A-A in FIG. 1A.

Referring to FIG. 1A of the drawings, an illustrative embodiment of an instrument lens cleaner according to the present disclosure is generally indicated by reference numeral 100. The instrument 100 includes a generally elongated, cylindrical or tubular sheath 105 having a sheath wall 110. Wall 110 may be a substantially rigid or semi-rigid plastic material. The sheath wall can also be flexible to accommodate a flexible scope. The tubular sheath 105 has a proximal end 125 and a distal end 130. A cross section of the sheath wall 110 at section A-A is shown in FIG. 4. Referring to FIG. 4, the sheath wall 110 typically has a generally annular cross-sectional configuration and defines a sheath interior 115 and a sheath exterior 120 which defines the outer surface of the sheath wall 110.

The tubular sheath 105 is dimensioned and configured to slidingly receive a conventional scope therein. The scope can be inserted into an already placed sheath or alternatively positioned within the sheath and together inserted into the body. The scope can be fully removed from the sheath if desired. The sheath can accommodate various types of scopes, including but not limited to laparoscopes, thoracoscopes, etc. For example, during video assisted thorascopic surgery, a thoracic port is inserted through the ribs to provide access to the thoracic cavity for access to lung or other tissue. A separate access is provided through the ribs to insert a scope to visualize the thoracic cavity during the surgical procedure. The sheath of the present disclosure can be utilized with the thoracoscope to maintain a clean lens to provide consistent visibility and imaging during the surgical procedure. The sheath can also be utilized with a flexible scope if composed of a sufficiently flexible material.

Referring back to FIG. 1A, a fluid conduit 140, provided on each side of the tubular sheath 105, has a generally annular cross-sectional configuration and is connected along the sheath exterior 120. The fluid conduits 140 each have a proximal end portion 145 and a distal end portion 150 having an opening 155. The fluid conduits 140 extend generally parallel to the longitudinal axis of the tubular sheath 105. Each fluid conduit 140 has a proximal inlet end that is in fluid communication with a fluid reservoir 165 and a distal outlet end at the opening 155. The outlet 155 can in some embodiments include a fluid discharge nozzle 180. The diameter or width of the fluid conduits 140 may in some embodiments be substantially equal to or slightly larger than the thickness of the sheath wall 110. As shown, preferably two fluid conduits 140 are provided, preferably identical and illustratively spaced about 180 degrees apart, although other spacings are also contemplated. A different number of fluid conduits could also be provided. If a flexible sheath is utilized for a flexible scope, the fluid conduits would also be composed of sufficiently flexible material.

Referring to FIG. 1B, the fluid conduit 140 is connected to the sheath exterior 120 by attachment clip 170. The attachment clip 170 is normally biased in the locking configuration with arms 171 in a closer position. The clip 170 is coupled to the fluid conduit 140 by bending the clip arms 171 outwardly as shown by the phantom lines and sliding the clip 170 over the fluid conduits 140. When the arms 171 are released, they return to their original state, applying a holding force against the fluid conduits 140.

Figure 5:
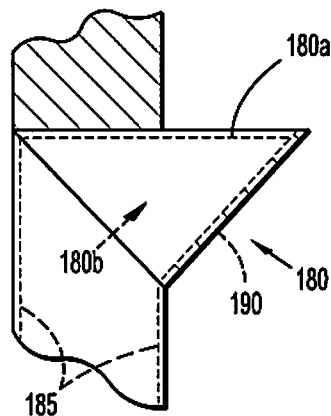
FIG. 5 is a cross-sectional view of a fluid discharge nozzle element of the scope lens cleaner according to an embodiment of the present disclosure.
Figure 6:
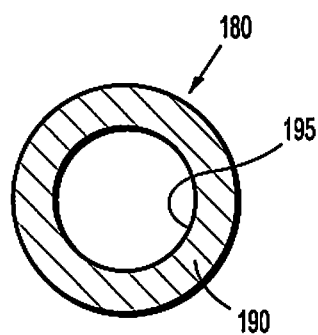
FIG. 6 is a cross-sectional view of an alternate embodiment of the fluid discharge nozzle of the present disclosure.

The fluid discharge nozzle 180 of each fluid conduit 140 communicates with the outlet end of the fluid conduit 140 and protrudes radially inwardly therein toward a longitudinal axis of the sheath in a direction toward the lens of a scope inserted through the sheath 105. As illustrated in FIG. 5, in one embodiment, the fluid discharge nozzle 180 has a nozzle wall 180a that is continuous with a wall 185 of the fluid conduit 140 and defines a nozzle interior 180b. The nozzle interior 180b of the fluid discharge nozzle 180 communicates with the fluid conduit 140. The wall 180a functions as a flow diverter to direct the fluid toward a nozzle plate 190. The nozzle plate 190 includes a plurality of spaced apart exit openings to deliver the cleaning fluid from reservoir 165 in a spray fashion. In an alternate embodiment illustrated in FIG. 6, a single nozzle opening 195 is formed in the nozzle plate, preferably extending through the central portion of the nozzle plate 190, to deliver the cleaning fluid in a single stream fashion. Other configurations for delivering the fluid are also contemplated.

Referring back to FIG. 1A, an elongated, flexible fluid connecting conduit 205, fitted with a conduit connector 210 at inlet end 160, is disposed in fluid communication with the inlet end of the fluid conduits 140. The conduit 205 in some embodiments is integral with the fluid conduits 140 and is therefore an extension thereof. In other embodiments, the conduit 205 is a separate tube connected to the fluid conduits 140. The fluid connecting conduit 205 is adapted for connection to a discharge outlet (not illustrated) of a fluid pump and supply apparatus 215, such as through the conduit connector 210. The fluid pump and supply apparatus 215 may be conventional and include the fluid reservoir 165 that is adapted to contain a cleaning fluid 200 such as saline solution. As shown, conduit 205 splits at region 207 so the cleaning fluid 200 is transported in the direction of the arrows through both fluid conduits 140 for discharge through associated nozzles 180.

Figure 3:
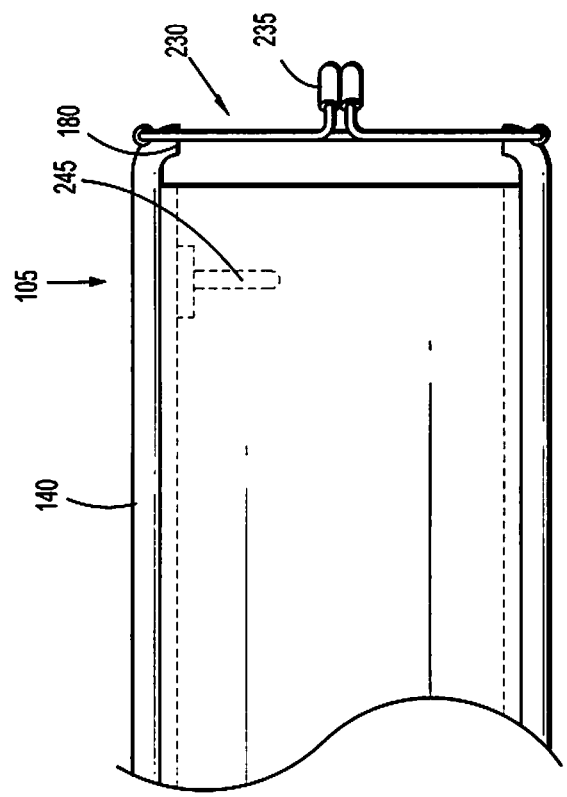
FIG. 3 is an enlarged side view of the scope lens cleaner of FIG. 1A.

A roller mechanism 230 (FIG. 2A) is connected to the distal end 130 of the elongated sheath exterior 120. As illustrated in FIGS. 2A-2B and 3, the roller mechanism 230 is connected adjacent the fluid discharge nozzles 180. The roller mechanism 230 includes two wiping arms 235, 238 of a material for wiping and cleaning the lens 265 of an endoscope 250 inserted through and extending distally from the tubular sheath 105.

The roller mechanism 230 in the illustrated embodiment is formed into a substantially ring shape as shown in FIG. 2B. Two arms 231, 233 extend inwardly from the ring-like member to form the wiping arms 235, 238, respectively. The roller mechanism can be formed of a wire or tubular member with a normal position of that shown in FIG. 2B. For example, it can be composed of a naturally sprung material or a shape memory material with a memorized position of FIG. 2B so it automatically returns to this position after the scope retraction described below. When the scope is advanced as described below, it forces the wiping arms 235, 258 to separate in a transverse sweeping motion over the lens to the position of FIG. 2A. When the scope is retracted, the wiping arms 235, 238 return to their normal (initial) position of FIG. 2B. The roller mechanism 230 includes two collars 255 which frictionally engage a respective recess 260 in the fluid conduit 140 to retain the roller mechanism 130.

The region adjacent the arms 231, 233 can be considered to function as levers 240. The levers 240 move between a non-cleaning position where the arms are adjacent (FIG. 2B) to a cleaning position where the arms separate to move across the lens of the scope (FIG. 2A). That is, in the cleaning position, the levers 240 swing away from the distal end 130 of the elongated sheath 105 and the wiping arms 235, 238 of roller 235 wipe across the endoscope lens 265 as illustrated in FIG. 2A. In other words, in the dispensing (cleaning) position, the swinging of the levers 240 in an arc enable arms 235, 238 to remove fluid 200 and/or debris from the surface of the endoscope lens. Note in the non-cleaning position, the levers 240 are positioned at an angle with respect to the longitudinal axis of the elongated sheath 105 as illustrated in FIG. 2B. The levers 240 are preferably normally in a non-cleaning position.

In one embodiment, an actuator 245 is in communication with each fluid conduit 140. Only one of the actuators is shown in the drawings. The actuators 245 enable the automatic delivery of cleaning fluid upon insertion of the scope 265 through the sheath 105. More specifically, the actuator is operatively connected to a valve (not shown). The valve provides for a cutoff of fluid to the discharge nozzle 180. When the scope 265 is in the advanced position of FIG. 2A to view the surgical site during surgery, the actuator 245 is in the pivoted position. To clean the scope of the lens, the scope 265 is retracted proximally within the sheath, thereby allowing actuator 245 to move to its position of FIG. 3. This opens the valve to allow fluid to be dispensed through the nozzles 180 as the actuator moves the valve. As the scope is re-advanced, it pivots actuator 245 to close the valve to cut off fluid flow. Consequently, in this embodiment, scope retraction enables the actuator 245 to open the valve to open the conduits 140 for fluid flow through the discharge nozzle and subsequent distal movement of the scope returns the actuator 245 to its original position and actuates the wiping arms 235, 238 to wipe and clean the surface of the lens 265 of scope 250. It is also contemplated that rather than the sequential operation of the valve and wiping arms, scope advancement could simultaneously open the nozzles for fluid flow and actuate the wiping arms 235, 238. Consequently, when the roller mechanism is in a cleaning position, the fluid conduit is in the dispensing state and when the roller mechanism is in a non-cleaning position, the fluid conduit is in the non-dispensing state.

As can be appreciated, the scope lens can therefore be cleaned in situ, i.e. without requiring withdrawal of the scope from the patient's body, as it can be cleaned by slight retraction and re-advancement multiple times during a surgical procedure.

Note in an alternate embodiment, the actuator can include a conduit engaging structure to pinch the fluid conduit(s) 140 to close it off to fluid flow. In this embodiment, movement of the scope would contact the actuator to pivot it so the conduit engaging structure would be released from pinching engagement with the fluid conduit 140 to enable the flow of cleaning fluid through the conduit 140 and through the nozzle. Thus, the actuator would switch the fluid discharge nozzle 180 between dispensing and non-dispensing states in response to scope movement within the elongated sheath 105.

Figure 2C:
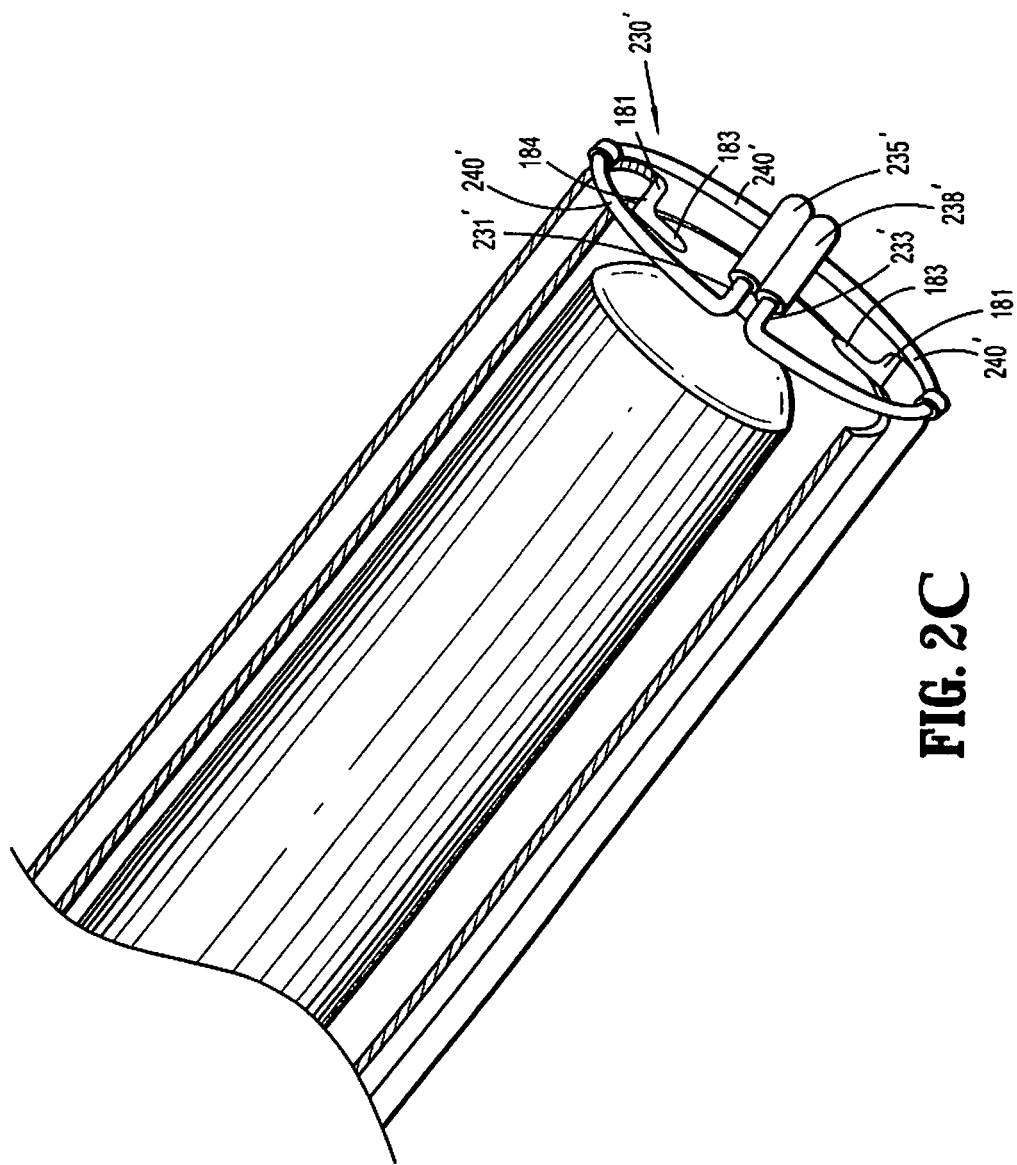
FIG. 2C is a view similar to FIG. 2B showing an alternate embodiment for opening the nozzle.

In another embodiment illustrated in FIG. 2C, the movement of the scope from the retracted position to the advanced position of FIG. 2B would move hinged nozzle covers to automatically open a valve. That is, hinges 181 are hingedly connected to the discharge nozzles and cover the discharge nozzles in their normal position. When the scope is advanced, the scope contacts arm 183 of each hinge to pivot the cover portion 184 away from the nozzle to provide an opening for fluid flow. In an alternate embodiment, the hinges are connected to the lever arms 240', so that when distal movement of the scope moves the lever arms, the cover of the hinges is moved away from the nozzle to open the nozzle for fluid flow. Otherwise, the wiper is the same as in FIG. 2B and includes roller mechanism 230' with arms 231', 233' and wiping arms 235', 238'.

In operation, as the endoscope 250 is moved distally relative to the elongated sheath 105, the endoscope 250 makes contact with the actuator 245 and as a result, the fluid discharge nozzle 180 automatically sprays an amount of fluid 200 onto the endoscope lens 265. The duration of the spray creates a mist onto the endoscope lens 265. As the endoscope continues to be advanced distally it contacts arms 235, 238 at roller 230 to pivot the arms 235, 238 to move transversely over the lens 265 to wipe the fluid 200 and/or debris from the surface of the lens 265. The endoscope continues to extend distally after the arms 235, 238 wipe the fluid 200 and/or debris and is out of the spray zone. The endoscope lens 265 captures images of the surgical field without having arms 235, 238 being in the camera field of view as the scope housing (body) maintains the arms 235, 238 in a spaced position (see FIG. 2A). If at any time during the surgical procedure the lens needs to be cleaned, the endoscope 250 can be withdrawn into the sheath 105, and then re-advanced to pivot the wiping arms 235, 238 to clean the lens 265 and to open the nozzle 180 in the embodiments having an actuator activated by scope movement.

Note in some embodiments, the fluid pump and supply apparatus 215 are selectively operated to pump a cleaning fluid 200, such as saline solution, through the fluid connecting conduit 205 and the fluid discharge nozzle 180. The cleaning fluid 200 can be discharged from the fluid discharge nozzle 180 through the nozzle openings in a spray pattern, or alternatively, through a single nozzle opening in a single stream pattern (or alternatively in other patterns), against and across the surface of the lens 265. Thus, when desired to clean the lens, the scope is retracted and the user actuates a pump or other device to advance the fluid through the conduit and nozzle. This is shown for example in the embodiment of FIG. 7. In other embodiments, as described above, rather than the user selectively pumping cleaning fluid, the endoscope movement would automatically deliver cleaning fluid to the lens.

Figure 7:
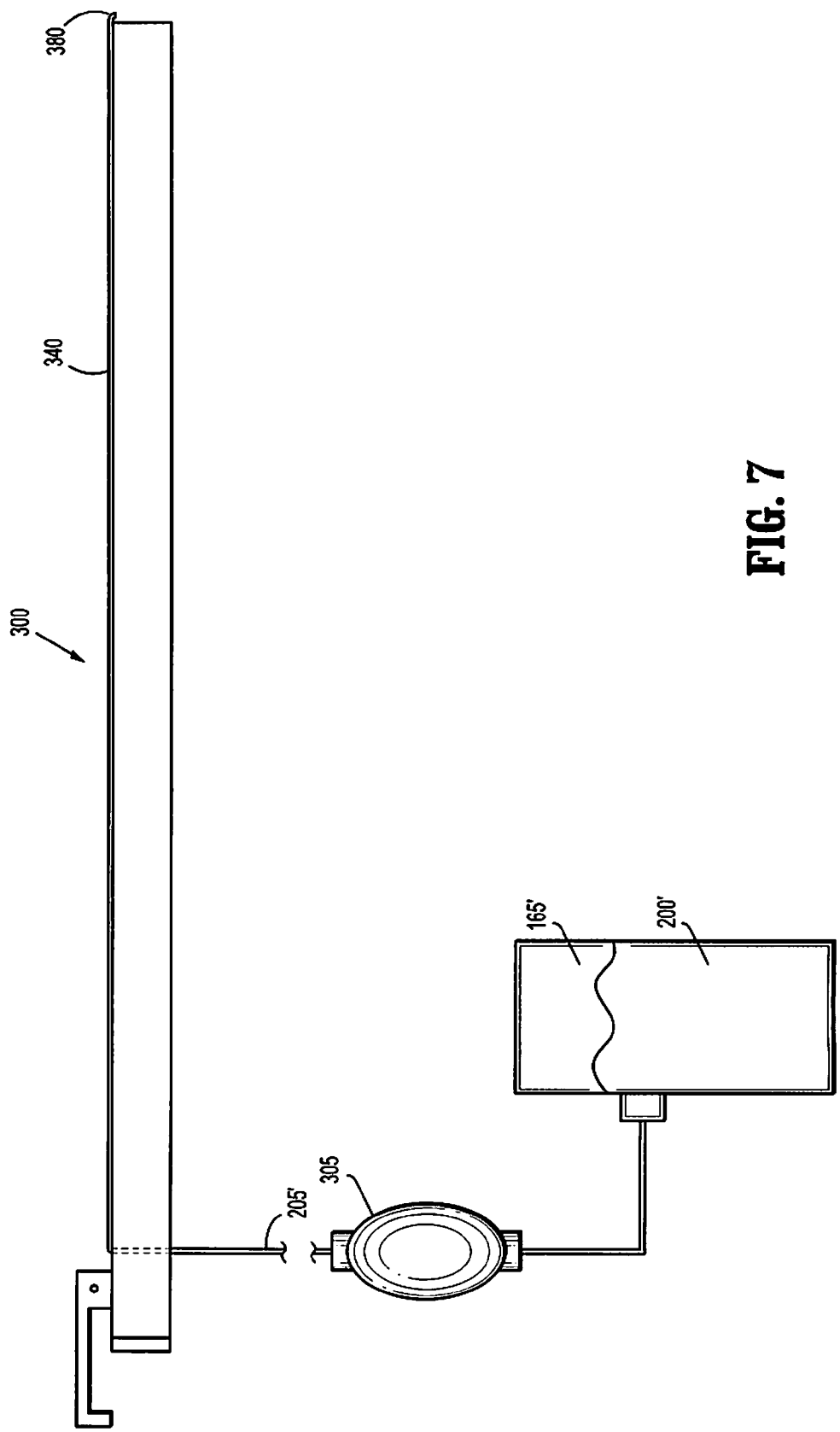
FIG. 7 is a schematic view of a scope lens cleaner according to another embodiment of the present disclosure.

In the embodiment of FIG. 7 the instrument lens cleaner 300 is similar to the instrument lens cleaner 100 of FIG. 1A, with the exception of the actuating system to spray the fluid 200'. The instrument lens cleaner 300 includes a bulb pump 305 to inject, e.g. to spray, the fluid 200' to clean the endoscope lens 265. In operation, a surgeon, when desired, manually squeezes the bulb 305 to discharge the cleaning fluid 200' under pressure from the fluid reservoir 165 and into the fluid connecting conduit 205'. Although one conduit 340 is shown in fluid communication with connecting conduit 205', two fluid conduits (or additional conduits) as in the embodiment of FIG. 1 are also contemplated. The conduit(s) 340 can include a pressure-release valve therein that is normally closed but opens when the bulb is squeezed to inject the fluid at high pressure. Thus, at sufficient pressure, the valve opens to enable fluid discharge nozzle 380 to release high-pressure but low volume fluid 200' such as saline. As the surgeon releases the bulb 305 to return to its initial position, the valve self-closes and the bulb 305 is refilled for the next shot of fluid. Note other types of liquid pumps could alternatively be provided. Note the scope can be withdrawn during use to place the lens adjacent the discharge nozzle for application of cleaning fluid. Advancement would then actuate the wiping arms in the manner described above.

Figure 8B:
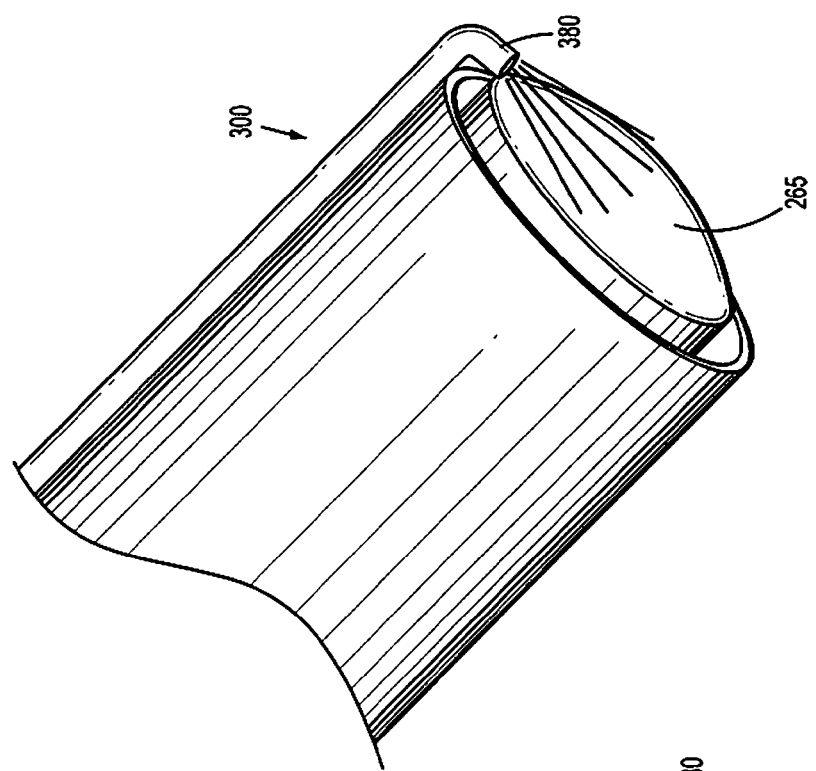
FIGS. 8A-8B are enlarged perspective views of the scope lens cleaner of FIG. 7.
Figure 8A:
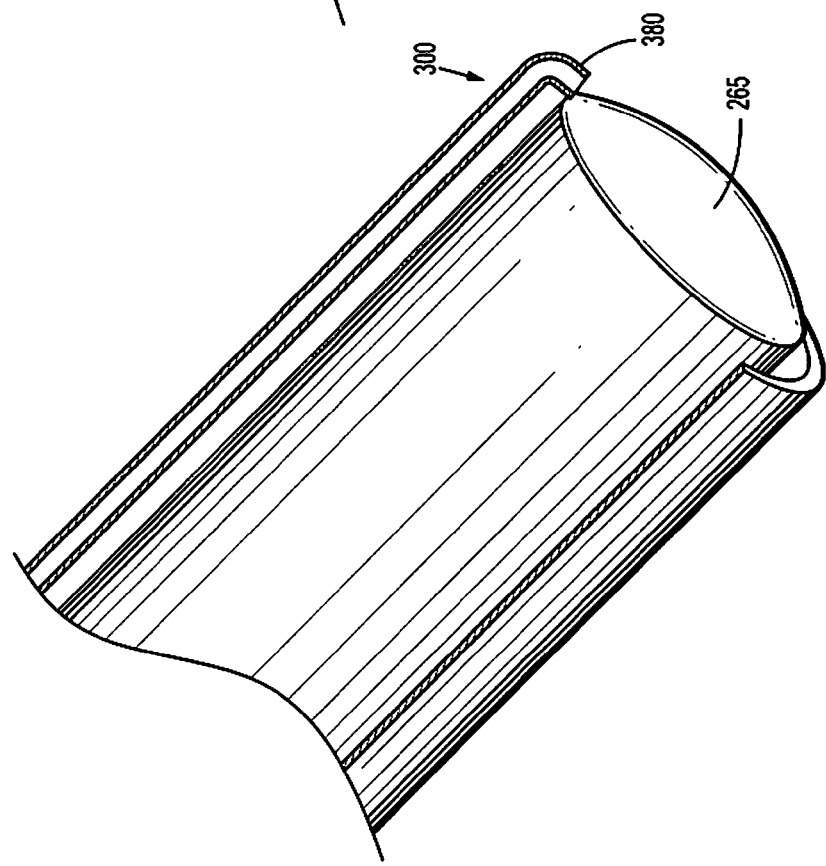

FIGS. 8A-8B are side, partially schematic views of the instrument lens cleaner 300 of FIG. 7. FIG. 8A illustrates the fluid discharge nozzle 380 prior to spraying cleaning fluid 200 on the scope lens 265. In response to the surgeon squeezing the bulb 305, the fluid discharge nozzle 380 sprays a mist (or jet or stream) of cleaning fluid on the scope lens 265 (FIG. 8B) to remove debris. It should be understood that other mechanisms beside the bulb 305 can be used to inject cleaning fluid 200', such as a foot pedal (not shown) or other hand-controlled device such as a syringe type mechanism or a trigger to control the discharge of cleaning fluid 200'. Automated or semi-automated delivery mechanisms can be provided. Also, as noted above, two fluid conduits 340 could be provided, with connecting conduit 205' split as in conduit 205 of FIG. 1A to deliver fluid to both conduits 340.

The lens cleaner 300 of FIGS. 7-8 includes a roller mechanism identical to that of FIG. 2A or identical to that of FIG. 2B. Such roller mechanism is not shown in FIGS. 7-8 for clarity.

In each of the embodiments herein, one or more fluid conduits with respective fluid openings or nozzles can be provided. The fluid can be delivered as a mist, spray, jet, stream, etc.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An instrument for cleaning a lens of a scope comprising:
   an elongated sheath having proximal and distal end portions, the elongated sheath having an interior and an exterior, the interior dimensioned and configured to slidingly receive the scope therein;
   a roller mechanism including:
   a pair of semi-circular supports defining a ring, each of the pair of semi-circular supports pivotally coupled to the distal end portion of the sheath about a pivot and including a support arm extending across a diameter of the ring; and
   a pair of wiping arms, each of the pair of wiping arms mounted on the respective support arm, the pair of wiping arms transitionable between a non-cleaning position in which the pair of wiping arms are adjacent to each other and a cleaning position in which the pair of wiping arms are radially spaced apart; and
   a fluid conduit for transporting fluid and having a fluid discharge opening to deliver fluid to the lens of the scope, the fluid conduit coupled to the exterior of the sheath,
   wherein the pair of wiping arms wipes across an entire surface of the lens during a transition from the non-cleaning position to the cleaning position.

2. The instrument of claim 1, wherein when the roller mechanism is in the cleaning position, the fluid conduit is in a dispensing state.

3. The instrument of claim 2, wherein when the roller mechanism is in the non-cleaning position, the fluid conduit is in a non-dispensing state.

4. The instrument of claim 3, wherein the roller mechanism transitions to the non-cleaning position when the scope retracts inside the interior of the sheath.

5. The instrument of claim 1, wherein advancement of the scope with respect to the sheath automatically discharges fluid through the discharge opening.

6. The instrument of claim 1, wherein advancement of the scope automatically discharges fluid through the discharge opening.

7. The instrument of claim 1, further comprising an attachment clip configured to attach the fluid conduit to the exterior of the sheath.

8. The instrument of claim 1, wherein the wiping arms move transversely over the scope lens.

9. The instrument of claim 1, further comprising a pump, the pump configured to switch between first and second positions, wherein in the first position the fluid conduit is open to deliver fluid and in the second position the fluid conduit is closed.

10. The instrument of claim 9, wherein the pump comprises a bulb pump actuated manually by squeezing the bulb pump.

11. The instrument of claim 1, wherein the fluid conduit includes a fluid discharge nozzle, the fluid discharge nozzle being normally closed.

12. The instrument of claim 1, wherein the pair of wiping arms maintains contact with the surface of the lens during the transition from the non-cleaning position to the cleaning position.

13. An instrument for cleaning a lens of a scope comprising:
   an elongated sheath having proximal and distal end portions, the elongated sheath having a sheath interior and a sheath exterior, the interior dimensioned and configured to slidably receive the scope therein;
   a pair of semi-circular supports defining a ring, each of the pair of semi-circular supports pivotally coupled to the distal end portion of the elongated sheath; and
   a pair of wiping arms, each of the pair of wiping arms extending across a diameter of the ring and movable from a first position in which the wiping arms are adjacent one another to a second position in which the wiping arms are spaced from one another, the wiping arms movable from the first position to the second position upon contact with the lens of the scope inserted through the sheath, wherein the pair of wiping arms wipes across an entire surface of the lens.

14. The instrument of claim 13, wherein the sheath comprises a fluid conduit for delivering a cleaning fluid to the lens of the scope inserted through the sheath.

15. The instrument of claim 13, wherein movement of the wiping arms opens a valve for delivering a cleaning fluid to the lens.

16. The instrument of claim 13, wherein movement of the scope opens a valve for delivering a cleaning fluid to the lens.

* * * * *